(12) United States Patent
Allen et al.

(10) Patent No.: US 9,011,818 B2
(45) Date of Patent: Apr. 21, 2015

(54) MATERIALS AND METHODS FOR BIOLOGICAL IMAGING

(75) Inventors: Peter M. Allen, Cambridge, MA (US); Wenhao Liu, Cambridge, MA (US); Moungi G. Bawendi, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 313 days.

(21) Appl. No.: 12/627,615

(22) Filed: Nov. 30, 2009

(65) Prior Publication Data

US 2011/0129420 A1 Jun. 2, 2011

(51) Int. Cl.
*A61K 49/00* (2006.01)
(52) U.S. Cl.
CPC .......... *A61K 49/0067* (2013.01); *Y10S 977/953* (2013.01); *Y10S 977/774* (2013.01)
(58) Field of Classification Search
CPC combination set(s) only.
See application file for complete search history.

(56) References Cited

U.S. PATENT DOCUMENTS

| 6,225,198 B1 | 5/2001 | Alivisatos et al. |
| 6,306,736 B1 | 10/2001 | Alivisatos et al. |
| 6,322,901 B1 | 11/2001 | Bawendi et al. |
| 6,855,202 B2 | 2/2005 | Alivisatos et al. |
| 7,181,266 B2 | 2/2007 | Frangolini et al. |
| 2005/0020922 A1 | 1/2005 | Frangolini et al. |
| 2006/0172133 A1* | 8/2006 | Naasani ........................ 428/403 |
| 2007/0103068 A1* | 5/2007 | Bawendi et al. ............. 313/506 |
| 2011/0037029 A1* | 2/2011 | Liu et al. ...................... 252/500 |

OTHER PUBLICATIONS

Zimmer et al. JACS 2006, 128, 2526-2527.*
Dabbousi et al. J Phys Chem B 1997, 101, 9463-9475.*
Liu et al. JACS 2007 129, 14530-14531.*
Gerion et al. J. Phys. Chem. B 2001, 105, 8861-8871.*
Lee et al. JACS 2007, 129, 12739-12735.*
Liu et al. JACS 2008, 130, 1274-1284.*
Fu et al. University of Califonia Berkely Dissertation (May 29, 2006).*
Wang D. Semiconductor nanocrystal quantum dots. 2008, 171-196.*
U.S. Appl. No. 61/234,305, filed Aug. 16, 2009, Liu et al.
Aaron R. Clapp, I. L. M., Hedi Mattoussi,, Förster Resonance Energy Transfer Investigations Using Quantum-Dot Fluorophores. *ChemPhysChem* 2006, 7, (1), 47-57.
Akerman et al., *PNAS*, 99: 12617-12621 (2002).
Aldana, J.; et al., *J. Am. Chem. Soc.* 2001, 123, 8844-8850.
Algar, W. R.; Krull, U. J., 2006, 22, 11346-11352.
Bentzen, E. L.; Tomlinson, I. D.; Mason, J.; Gresch, P.; Warnement, M. R.; Wright, D.; Sanders-Bush, E.; Blakely, R.; Rosenthal, S. J., Surface modification to reduce nonspecific binding of quantum dots in live cell assays. *Bioconjugate Chemistry* 2005, 16, (6), 1488-1494.
Brown, E. B.; Campbell, R. B.; Tsuzuki, Y.; Xu, L.; Carmeliet, D.; Fukumura, D.; Jain, R. K. *Nat. Med.* 2001, 7, 864-868.
Bruchez et al., *Science*, 281: 2013-2016 (1998).
Cao, Y.; Banin, U. *J. Am. Chem. Soc.* 2000, 122, 9692-9702.
Cerussi et al., *Acad. Radiol.*, 8: 211-218 (2001).
Chan and Nie *Science*, 281: 2016-2018 (1998).
Chan et al., *Curr. Opin. Biotechnol.*, 13: 40-46 (2002).
Cheong et al., *IEEE J. Quantum Electronics*, 26:2166-2195 (1990).
Chiefari, J.; Chong, Y. K.; Ercole, F.; Krstina, J.; Jeffery, J.; Le, T. P. T.; Mayadunne, R. T. A.; Meijs, G. F.; Moad, C. L.; Moad, G.; Rizzardo, E.; Thang, S. H., Living free-radical polymerization by reversible addition-fragmentation chain transfer: The RAFT process. *Macromolecules* 1998, 31, (16), 5559-5562.
Choi, H. S.; Ipe, B. I.; Misra, P.; Lee, J. H.; Bawendi, M. G.; Frangioni, J. V. *Nano Letters* 2009, 9, 2354-2359.
Dahan, M.; Levi, S.; Luccardini, C.; Rostaing, P.; Riveau, B.; Triller, A., Diffusion Dynamics of Glycine Receptors Revealed by Single-Quantum Dot Tracking. *Science* 2003, 302, (5644), 442-445.
Gerion et al., *J. Am. Chem. Soc.*, 124: 7070-7074 (2002).
Goldman et al., *Anal.. Chem.*, 74: 841-847 (2002).
Goldman, E. R.; et al., *J. Am. Chem. Soc.* 2002, 124, 6378-6382.
Groc, L.; Heine, M.; Cognet, L.; Brickley, K.; Stephenson, F. A.; Lounis, B.; Choquet, D., Differential activity-dependent regulation of the lateral mobilities of AMPA and NMDA receptors. *Nat. Neurosci.* 2004, 7, (7), 695-696.
Howarth, M.; Chinnapen, D. J. F.; Gerrow, K.; Dorrestein, P. C.; Grandy, M. R.; Kelleher, N. L.; El-Husseini, A.; Ting, A. Y., A monovalent streptavidin with a single femtomolar biotin binding site. *Nat Meth* 2006, 3, (4), 267-273.
Howarth, M.; Liu, W.; Puthenveetil, S.; Meng, Y.; Marshall, L. F.; Schmidt, M. M.; Wittrup, K. D.; Bawendi, M. G.; Ting, A. Y. *Nat Meth* 2008, 5, 397-399.
Howarth, M.; Takao, K.; Hayashi, Y.; Ting, A. Y. *Proc Natl Acad Sci USA.* 2005, 102, 7583-7588.
Howarth, M.; Ting, A. Y. *Nature Protocols* 2008, 3, 534-545.
Jaiswal et al., *Nature Biotechnol.*, 21: 47-51 (2002).
Kim, S.; Bawendi, M. G., *J. Am. Chem. Soc.* 2003, 125, 14652-14653.
Klarreich, *Nature*, 413: 450-452 (2001).
Li, J. J.; Wang, Y. A.; Guo, W. Z.; Keay, J. C.; Mishima, T. D.; Johnson, M. B.; Peng, X.G. *J. Am. Chem. Soc.* 2003, 125, 12567-12575.
Liu, W.; Greytak, A. B.; Lee, J.; Wong, C. R.; Park, J.; Marshall, L. F.; Jiang, W.; Ting, A. Y.; Nocera, D. G.; Fukumura, D.; Jain, R. K.; Bawendi, M. G. *J. Am. Chem. Soc.* 2009, submitted.
Liu, W.; Howarth, M.; Greytak, A. B.; Zheng, Y.; Nocera, D. G.; Ting, A. Y.; Bawendi, M. G. *J. Am. Chem. Soc.* 2008, 130, 1274-1284.
Mattoussi, H.; et al, *J. Am. Chem. Soc.* 2000, 122, 12142-12150.
Medintz, I. L., *Nature Mater.* 2003, 2, 630-638.

(Continued)

*Primary Examiner* — Michael G. Hartley
*Assistant Examiner* — Sean R Donohue
(74) *Attorney, Agent, or Firm* — Steptoe & Johnson LLP

(57) ABSTRACT

Water soluble InAs(ZnCdS) semiconductor nanocrystals with bright and stable emission in the near infrared (NIR) wavelength range have been prepared. The NIR semiconductor nanocrystals can be functionalized to enable imaging of specific cellular proteins. In addition, the utility of the NIR region for in vivo biological imaging is clearly demonstrated by the superior ability of InAs(ZnCdS) semiconductor nanocrystals to image tumor vasculature.

7 Claims, 3 Drawing Sheets

(56) References Cited

OTHER PUBLICATIONS

Medintz, I. L.; Pons, T.; Delehanty, J. B.; Susumu, K.; Brunel, F. M.; Dawson, P. E.; Mattoussi, H., Intracellular delivery of quantum dot-protein cargos mediated by cell penetrating peptides. *Bioconjugate Chemistry* 2008, 19, (9), 1785-1795.

Murray, C. B.; Norris, D. J.; Bawendi, M. G. *J. Am. Chem. Soc.* 1993, 115, 8706-8715.

Nakayama et al., *Molecular Imaging*, 1: 365-377 (2002).

Parak, W. J.; et al., 2002, 14, 2113-2119.

Pathak et al., *J. Am. Chem. Soc.*, 123: 4103-4104 (2001).

Pons, T.; et al, *J. Phys. Chem. B* 2006, 110, 20308-20316.

Rosenthal et al., *J. Am. Chem. Soc.*, 124: 4586-4594 (2002).

Sapsford, K. E.; Pons, T.; Medintz, I. L.; Higashiya, S.; Brunel, F. M.; Dawson, P. E.; Mattoussi, H., Kinetics of Metal-Affinity Driven Self-Assembly between Proteins or Peptides and CdSe—ZnS Quantum Dots. *J. Phys. Chem. C.* 2007, 111, (11528-11538).

Smith, A. M.; Duan, H.; Rhyner, M. N.; Ruan, G.; Nie, S., A systematic examination of surface coatings on the optical and chemical properties of semiconductor quantum dots. *Phys. Chem. Chem. Phys.* 2006, 8, 3895-3903.

Snee, P. T.; Chan, Y.; Nocera, D. G.; Bawendi, M. G. *Adv. Mater.* 2005, 17, 1131-1136.

Uyeda, H. T.; et al., *J. Am. Chem. Soc.* 2005, 127, 3870-3878.

Vakoc, B. J.; Lanning, R. M.; Tyrrell, J. A.; Padera, T. P.; Bartlett, L. A.; Stylianopoulos, T.; Munn, L. L.; Teamey, G. J.; Fukumura, D.; Jain, R. K.; Bouma, B. E. *Nat Med* 2009, *advance online publication*.

Wang, Y.A., et al., 2002 *J. Am. Chem. Soc* 124, 2293.

Wu, X.; Liu, H.; Liu, J.; Haley, K. N.; Treadway, J. A.; Larson, J. P.; Ge, N.; Peale, F.; Bruchez, M. P., Immunofluorescent labeling of cancer marker Her2 and other cellular targets with semiconductor quantum dots. *Nature Biotechnol.* 2003, 21, (1), 41-46.

Xie, R.; Kolb, U.; Li, J.; Basche, T.; Mews, A. *J. Am. Chem. Soc.* 2005, 127, 7480-7488.

Xie, R.; Peng, X. *Angew. Chem.* 2008, 47, 7677-7680.

Xue, F.; et al., *Journal of Fluorescence* 2007, 17, 149-154.

Yan Zhang; et al., *Angew. Chem. Int. Ed.* 2006, 45, 4936-4940.

Yildiz, I.; McCaughan, B.; Cruickshank, S. F.; Callan, J. F.; Raymo, F. i. M., Biocompatible CdSe—ZnS Core-Shell Quantum Dots Coated with Hydrophilic Polythiols. *Langmuir* 2009, 25, (12), 7090-7096.

Zaheer et al., *Nature Biotechnol.*, 19: 1148-1154 (2001).

\* cited by examiner

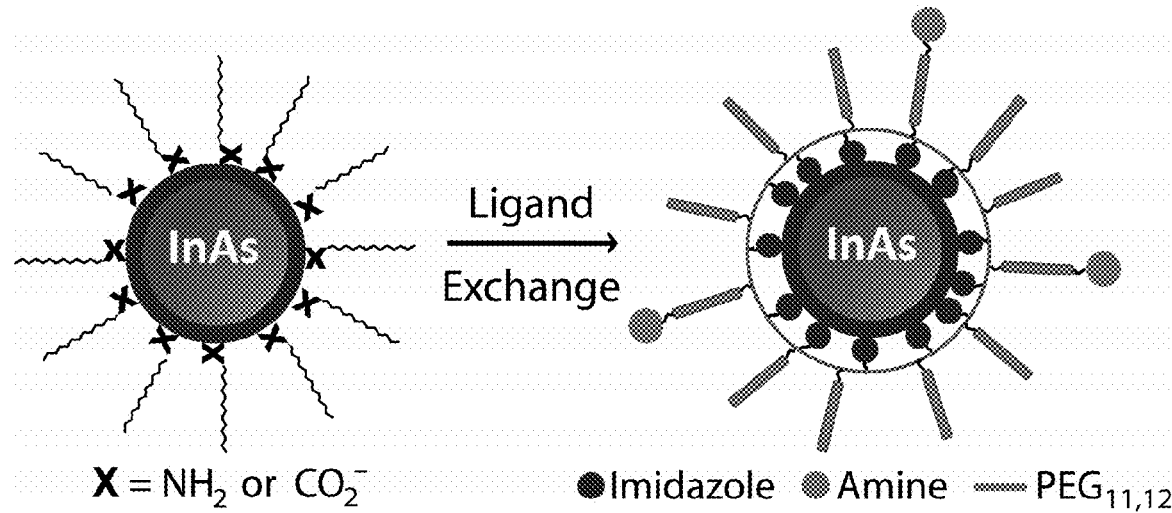
FIGURE 1
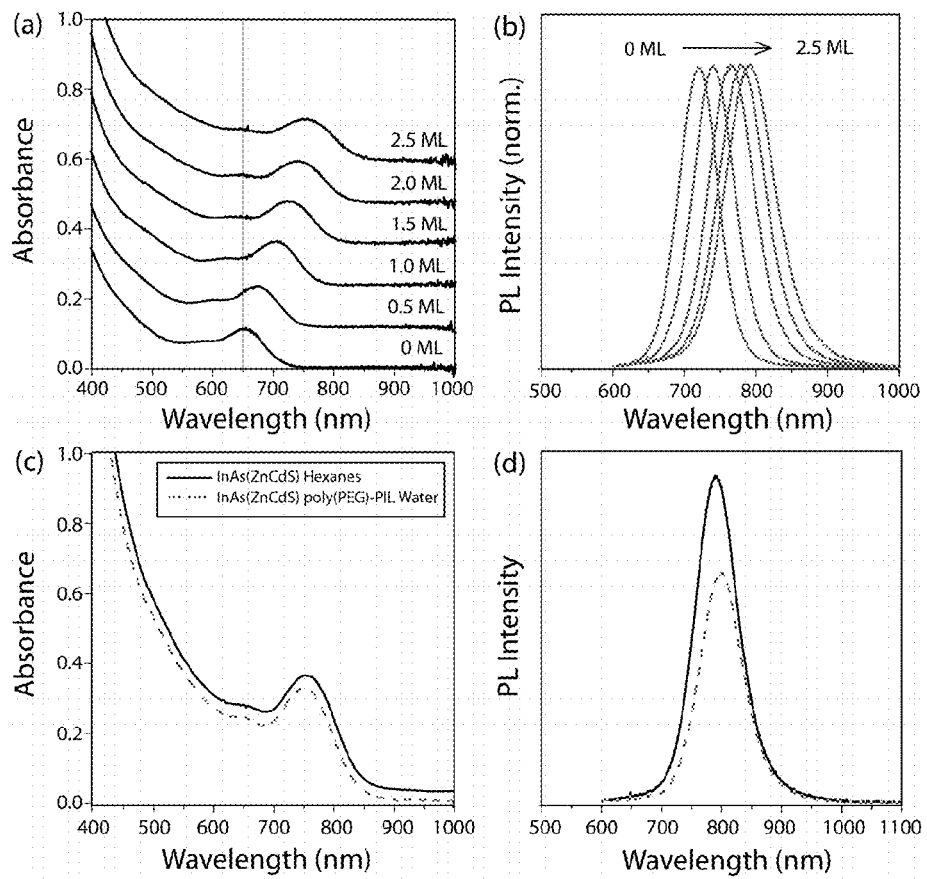
FIGURE 2A-D

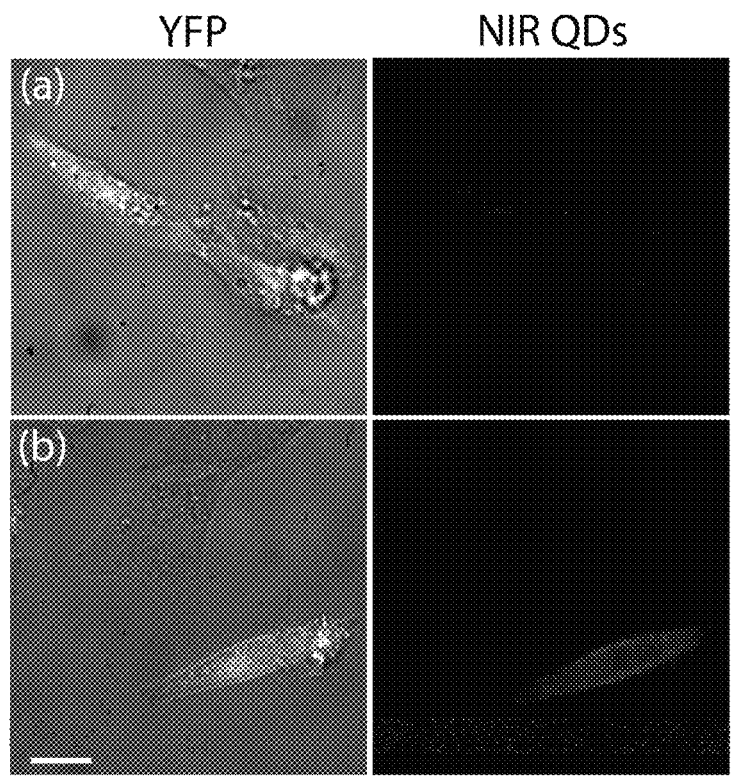
FIGURE 3A-B
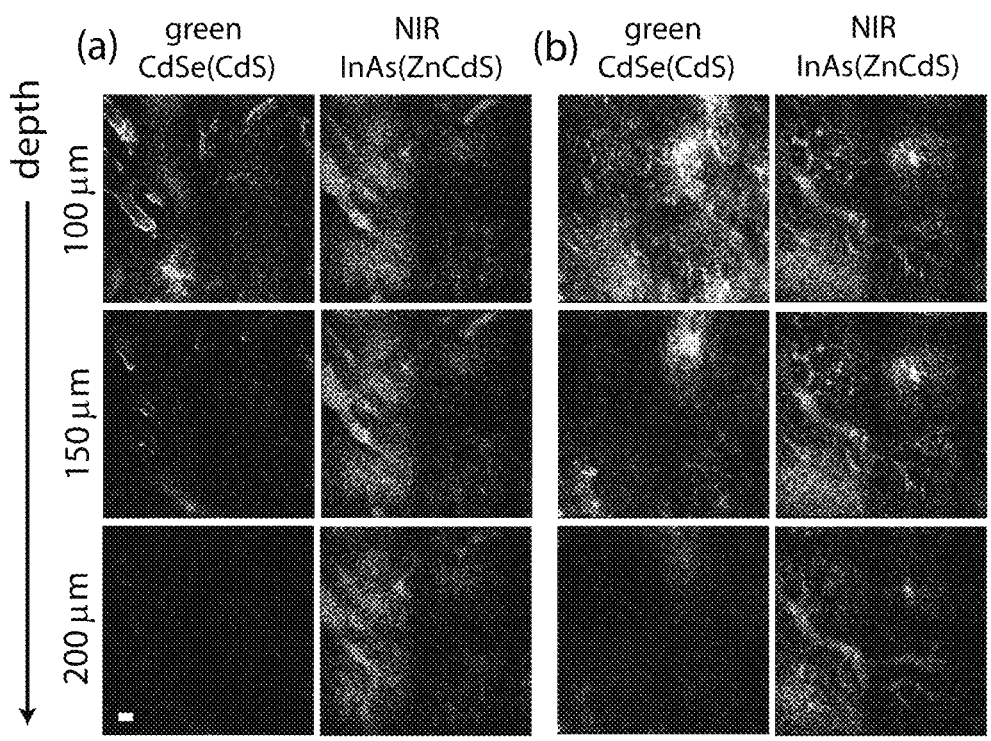
FIGURE 4A-B

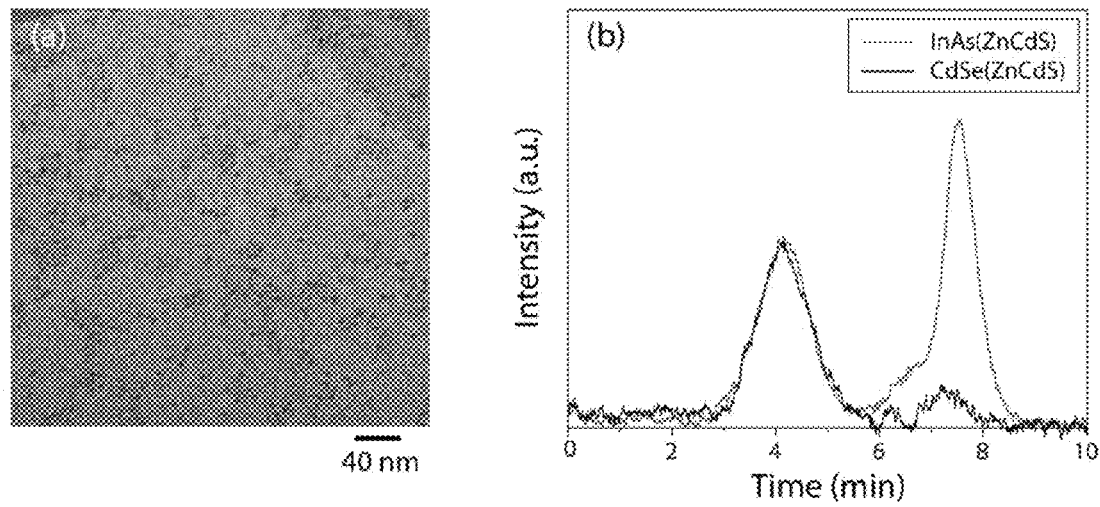
FIGURE 5A-B
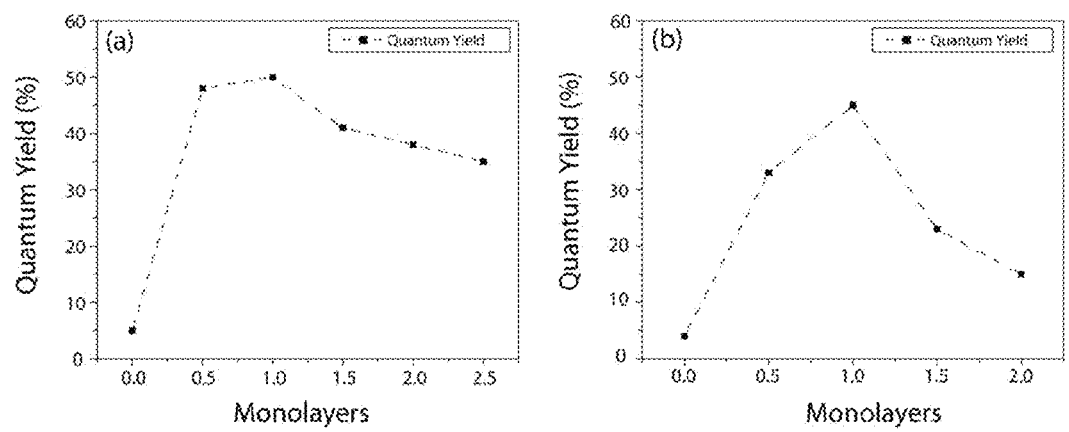
FIGURE 6A-B

MATERIALS AND METHODS FOR BIOLOGICAL IMAGING

FEDERALLY SPONSORED RESEARCH OR DEVELOPMENT

This invention was made with government support under Grant Nos. 1U54-CA119349 and R01-CA126642, awarded by the National Institutes of Health, and Grant No. W911NF-07-D-0004, awarded by the U.S. ARO. The government has certain rights in this invention.

TECHNICAL FIELD

The present invention relates to materials and methods for biological imaging.

BACKGROUND

Nanocrystals having small dimensions can have properties intermediate between molecular and bulk forms of matter. For example, nanocrystals of semiconductor materials having sufficiently small dimensions can exhibit quantum confinement of excitons (excited state electron-hole pair) in all three dimensions. Quantum confinement leads to an increase in the effective band gap of the material with decreasing crystallite size. Consequently, both the optical absorption and emission of nanocrystals shift to the blue (i.e., to higher energies) as the size of the nanocrystal decreases.

The quantum efficiency of emission from nanocrystals having a core of a first semiconductor material can be enhanced by applying an overcoating of a second semiconductor material such that the conduction band of the second semiconductor material is of higher energy than that of the first semiconductor material, and the valence band of the second semiconductor material is of lower energy than that of the first semiconductor material. As a result, both charge carriers of an exciton, i.e., electrons and holes, are confined in the core of the nanocrystal.

SUMMARY

In one aspect, a composition for biological imaging includes a water soluble semiconductor nanocrystal having a hydrodynamic diameter of no greater than 10 nm and having a peak emission wavelength in the range of 700 nm to 1000 nm.

The semiconductor nanocrystal can have a core including a first semiconductor material, where the first semiconductor material is a III-V semiconductor. The core can have a diameter of 1.4 nm or less. The semiconductor nanocrystal can include a shell on a surface of the core, the shell including a second semiconductor material, where the second semiconductor material can be a II-VI semiconductor. The II-VI semiconductor can include a II-VI semiconductor alloy. The first semiconductor material can be InAs and the II-VI semiconductor alloy can be a ZnCdS alloy.

The semiconductor nanocrystal can include a polymeric ligand. The polymeric ligand can include a poly(ethylene) glycol. The polymeric ligand can be poly(amino-$PEG_{11}$)$_{25\%}$-PIL. The semiconductor nanocrystal can include a ligand having at least one selectively reactive functional group or at least one selectively binding functional group.

In another aspect, a method of in vitro biological labeling includes coupling a water soluble semiconductor nanocrystal to a first compound having a first selectively binding functional group, thereby forming a nanocrystal conjugate, where the semiconductor nanocrystal has a hydrodynamic diameter of no greater than 10 nm and has a peak emission wavelength in the range of 700 nm to 1000 nm, contacting the nanocrystal conjugate with a cell, where the cell includes a second compound, where the second compound includes a selective binding counterpart to the first selectively binding functional group, and where contacting includes forming an affinity complex between the first selectively binding functional group and the selective binding counterpart and visualizing the nanocrystal conjugate affinity complex.

The first compound can include an avidin, a streptavidin, an avidin-bound compound, or a strepavidin-bound compound. The second compound can include a biotin moiety.

In another aspect, a method of in vivo biological imaging includes contacting a semiconductor nanocrystal with a tissue of a living subject, where the semiconductor nanocrystal has a hydrodynamic diameter of no greater than 10 nm and has a peak emission wavelength in the range of 700 nm to 1000 nm, and visualizing the nanocrystal.

Visualizing can include multiphoton microscopy. Visualizing can include recording an image at a tissue depth of 0 µm to greater than 200 µm. Visualizing can include recording an image at a tissue depth of at least 150 µm and no greater than 200 µm.

The details of one or more embodiments are set forth in the accompanying drawings and the description below. Other features, objects, and advantages will be apparent from the description and drawings, and from the claims.

DESCRIPTION OF DRAWINGS

FIG. 1 is a schematic representation the ligand exchange of organic soluble nanocrystals with poly(amino-$PEG_{11}$)$_{25\%}$-PIL to enable water solublization.

FIG. 2A is a graph depicting absorbance of InAs ($Zn_{0.7}Cd_{0.3}S$) during shell growth from 0-2.5 monolayers (MLs).

FIG. 2B is a graph depicting photoluminescence of InAs ($Zn_{0.7}Cd_{0.3}S$) during shell growth from 0-2.5 MLs.

FIG. 2C is a graph depicting absorbance of InAs ($Zn_{0.7}Cd_{0.3}S$) in hexanes (solid) and after ligand exchange with poly(amino-$PEG_{11}$)$_{25\%}$-PIL (dotted) in PBS at pH 7.4.

FIG. 2D is a PL ($\lambda_{max}$=795 nm, fwhm=82 nm) graph of InAs($Zn_{0.7}Cd_{0.3}S$) in hexanes (solid) and after ligand exchange with poly(amino-$PEG_{11}$)$_{25\%}$-PIL (dotted) in PBS at pH 7.4.

FIG. 3 includes images of HeLa cells expressing yellow fluorescent protein (YFP) fused to a biotinylated peptide presented on the extracellular membrane wherein (a) the streptavidin-nanocrystals pre-blocked with biotin did not bind to the cell surface and; (b) non-blocked streptavidin-nanocrystals are bound to the surface of YFP-expressing cells (scale bar, 1 µm).

FIG. 4 includes in vivo grayscale MPM images with 850 nm excitation (a-b) of the vasculature in a mammary tumor in a mouse with CdSe(CdS) (green channel) and InAs(ZnCdS) (NIR channel) poly($PEG_{12}$)-PIL nanocrystals injected intravenously and imaged simultaneously (scale bar, 100 µm).

FIG. 5A is a TEM image of InAs(ZnCdS) nanocrystals with inorganic size ~2.9 nm drop-cast from water.

FIG. 5B is a gel filtration chromatogram of InAs(ZnCdS) poly($PEG_{12}$)-PIL with a retention time of 4.17 minutes corresponding to a hydrodynamic diameter (HD) of <10 nm (the peak at 7.5 minutes corresponds to free poly($PEG_{12}$)-PIL ligand) and CdSe(CdS) poly($PEG_{12}$)-PIL nanocrystals with a retention time of 4.10 minutes corresponding to a HD of <10 nm.

FIG. 6A is a graph depicting quantum yield (QY) as a function of ZnCdS shell growth on InAs cores with the addition of oleyl amine.

FIG. 6B is a graph of QY as a function of ZnCdS shell growth on InAs cores without the addition of oleyl amine. The decrease in QY is likely the result of decreased surface passivation as residual In(Myr)$_3$ is consumed by the highly reactive over-coating precursors.

DETAILED DESCRIPTION

Fluorescent semiconductor nanocrystals are excellent imaging agents for biomedical assays and imaging. A unique property of semiconductor nanocrystals is that their absorbance increases with increasing separation between excitation and emission wavelengths. Much of the enthusiasm for using semiconductor nanocrystals in vivo stems from this property, since photon yield should be proportional to the integral of the broadband absorption. Tissue scatter and absorbance can sometimes offset increasing semiconductor nanocrystal absorption at bluer wavelengths, and counteract this potential advantage. By using a previously validated mathematical model, the effects of tissue absorbance, tissue scatter, wavelength dependence of the scatter, water to hemoglobin ratio, and tissue thickness on semiconductor nanocrystal performance was explored. When embedded in biological fields and tissues, semiconductor nanocrystal excitation wavelengths can be quite constrained, and that excitation and emission wavelengths should be selected carefully based on the particular application.

Semiconductor nanocrystals are inorganic fluorophores that are currently being investigated for use as luminescent biological probes due to their nanometer dimensions and unique optical properties. Compared to conventional fluorophores and organic dyes, semiconductor nanocrystals have a number of attractive characteristics including high absorption cross-section, broadband absorption that increases at blue wavelengths, relatively narrow and symmetric luminescent bands, simultaneous excitation of semiconductor nanocrystals with different emission wavelengths using a single excitation wavelength, and resistance to photo-degradation. Altering the surface chemistry can provide the nanocrystals with other useful properties, such as aqueous solubility and the ability to conjugate with biomolecules such as proteins, oligonucleotides, antibodies, and small molecule ligands. Such "targeted" semiconductor nanocrystals have been reported as imaging agents for nucleic acid hybridization, cellular imaging, immunoassays, and recently, tissue-specific homing in vivo. See, for example, Bruchez et al., *Science*, 281: 2013-2016 (1998); Chan and Nie *Science*, 281: 2016-2018 (1998); Mattousi et al., *J. Am. Chem. Soc.*, 122: 12142-12150 (2000); Klarreich, *Nature*, 413: 450-452 (2001); Chan et al., *Curr. Opin. Biotechnol.*, 13: 40-46 (2002); Wu et al., *Nature Biotechnol.*, 21: 41-46 (2003); Dubertret et al., *Science*, 298: 1759-1762; Pathak et al., *J. Am. Chem. Soc.*, 123: 4103-4104 (2001); Gerion et al., *J. Am. Chem. Soc.*, 124: 7070-7074 (2002); Goldman et al., *J. Am. Chem. Soc.*, 124: 6378-6382 (2002); Goldman et al., *Anal. Chem.*, 74: 841-847 (2002); Rosenthal et al., *J. Am. Chem. Soc.*, 124: 4586-4594 (2002); Akerman et al., *PNAS*, 99: 12617-12621 (2002); and Jaiswal et al., *Nature Biotechnol.*, 21: 47-51 (2002), each of which is incorporated by reference in its entirety.

In vivo imaging applications, such as, for example, reflectance fluorescent imaging, can require deep photon penetration into and out of tissue. In living tissue, total photon attenuation is the sum of attenuation due to absorbance and scatter. Scatter describes the deviation of a photon from the parallel axis of its path, and can occur when the tissue inhomogeneity is small relative to wavelength (Rayleigh-type scatter), or roughly on the order of wavelength (Mie-type scatter). For inhomogeneities at least ten times less than the wavelength, Rayleigh-type scatter is proportional to the reciprocal $4^{th}$ power of wavelength. For example, in rat skin, scatter is proportional to $\lambda^{-2.8}$, suggesting strong wavelength-dependence, however, in post-menopausal human breast, scatter is proportional to $\lambda^{-0.6}$, suggesting weak wavelength-dependence. See, for example, Zaheer et al., *Nature Biotechnol.*, 19: 1148-1154 (2001); Nakayama et al., *Molecular Imaging*, 1: 365-377 (2002); Cheong et al., *IEEE J. Quantum Electronics*, 26:2166-2195 (1990); and Cerussi et al., *Acad. Radiol.*, 8: 211-218 (2001), each of which is incorporated by reference in its entirety.

Given the relatively low absorbance and scatter of living tissue in the near-infrared (NIR) region of the spectrum, considerable attention has focused on NIR fluorescence contrast agents. The near-infrared includes, but is not limited to, wavelengths in the range of 700 nm to 1000 nm. For example, conventional NIR fluorophores with peak emission between 700 nm and 800 nm have been used for in vivo imaging of protease activity, somatostatin receptors, sites of hydroxylapatite deposition, and myocardial vascularity, to name a few. Previous work has shown a particular NIR semiconductor nanocrystal synthesized and used for real-time in vivo vascular imaging. See, for example, U.S. Pat. No. 7,181,266 and U.S. Patent Application Publication No. 2005/0020922, each of which is incorporated by reference in its entirety.

A major barrier towards the wide-spread use of semiconductor nanocrystals biological fluorescent tags has been the difficulty in simultaneously optimizing a number of desirable nanocrystal properties: small size, high stability (both over time and in a wide pH range), high quantum yield, facile derivatizabilty, and low non-specific binding. Commercially available nanocrystals encapsulated with amphiphlic polymer coatings can be easily derivatized and are suitable for single molecule imaging, but can have sizes in the range of 20 nm to 30 nm in diameter. Nanocrystals that large can have limited access to crowded regions such as the neuronal synapse, and potentially alter the native behavior of labeled receptors. See, for example, Dahan, M.; Levi, S.; Luccardini, C.; Rostaing, P.; Riveau, B.; Triller, A., Diffusion Dynamics of Glycine Receptors Revealed by Single-Quantum Dot Tracking. *Science* 2003, 302, (5644), 442-445; Wu, X.; Liu, H.; Liu, J.; Haley, K. N.; Treadway, J. A.; Larson, J. P.; Ge, N.; Peale, F.; Bruchez, M. P., Immunofluorescent labeling of cancer marker Her2 and other cellular targets with semiconductor quantum dots. *Nature Biotechnol.* 2003, 21, (1), 41-46; Smith, A. M.; Duan, H.; Rhyner, M. N.; Ruan, G.; Nie, S., A systematic examination of surface coatings on the optical and chemical properties of semiconductor quantum dots. *Phys. Chem. Chem. Phys.* 2006, 8, 3895-3903; Howarth, M.; Chinnapen, D. J. F.; Gerrow, K.; Dorrestein, P. C.; Grandy, M. R.; Kelleher, N. L.; El-Husseini, A.; Ting, A. Y., A monovalent streptavidin with a single femtomolar biotin binding site. *Nat Meth* 2006, 3, (4), 267-273; Howarth, M.; Takao, K.; Hayashi, Y.; Ting, A. Y., Targeting quantum dots to surface proteins in living cells with biotin ligase. *Proc Natl Acad Sci USA.* 2005, 102, (21), 7583-7588; and Groc, L.; Heine, M.; Cognet, L.; Brickley, K.; Stephenson, F. A.; Lounis, B.; Choquet, D., Differential activity-dependent regulation of the lateral mobilities of AMPA and NMDA receptors. *Nat. Neurosci.* 2004, 7, (7), 695-696, each of which is incorporated by reference in its entirety.

Furthermore, amphiphilic polymer coatings are often highly charged, which contributes to non-specific binding to cell membranes. Non-specific binding interferes with single-particle imaging, where low background is essential. Non-specific adsorption can be mitigated via PEGylation of polymer-encapsulated nanocrystals, but this further increases nanoparticle size (see, e.g., Bentzen, E. L.; et al., *Bioconjugate Chem.* 2005, 16, 1488-1494, which is incorporated by reference in its entirety). Nanocrystals coated with phospholipids or silica shells have also been used in biological systems, but suffer from similar limitations of inherently large size and the need for a bulky PEG passivating layer. See, for example, Dubertret, B.; et al., *Science* 2002, 298, 1759-1762; and Parak, W. J.; et al., 2002, 14, 2113-2119, each of which is incorporated by reference in its entirety.

Small, water-soluble, and derivatizable nanocrystals can be prepared by displacing the native hydrophobic coating with carboxylate-bearing small molecule coordinating ligands such as mercaptoacetic acid (MAA). See, e.g., Aldana, J.; et al., *J. Am. Chem. Soc.* 2001, 123, 8844-8850; Mattoussi, H.; et al., *J. Am. Chem. Soc.* 2000, 122, 12142-12150; Kim, S.; Bawendi, M. G., *J. Am. Chem. Soc.* 2003, 125, 14652-14653; and Algar, W. R.; Krull, U. J., 2006, 22, 11346-11352, each of which is incorporated by reference in its entirety). Although such nanocrystals have hydrodynamic diameters (HDs) of only-6-8 nm, they can be inherently unstable due to weak ligand-nanocrystal interactions, leading to nanocrystal precipitation on the time scale of several hours under ambient conditions. See, for example, Smith, A. M.; et al., *Phys. Chem. Chem. Phys.* 2006, 8, 3895-3903; and Aldana, J.; et al., *J. Am. Chem. Soc.* 2001, 123, 8844-8850, each of which is incorporated by reference in its entirety. In addition, the ionization of the carboxylate group required to render the nanocrystals water dispersable results in instability under acidic conditions and also promotes non-specific binding to cells (Bentzen, E. L.; et al., *Bioconjugate Chem.* 2005, 16, 1488-1494; and Xue, F.; et al., *Journal of Fluorescence* 2007, 17, 149-154, each of which is incorporated by reference in its entirety). Moreover, nanocrystals ligand-exchanged with such mono-thiol based ligands typically suffer a dramatic decrease in quantum yield (Smith, A. M.; et al., *Phys. Chem. Chem. Phys.* 2006, 8, 3895-3903, which is incorporated by reference in its entirety). Dithiol ligands, such as dihydrolipoic acid (DHLA), are much more stable with respect to ligand dissociation, but still yield nanocrystals that precipitate under weakly acidic conditions. See, for example, Mattoussi, H.; et al, *J. Am. Chem. Soc.* 2000, 122, 12142-12150; and Pons, T.; et al, *J. Phys. Chem. B* 2006, 110, 20308-20316, each of which is incorporated by reference in its entirety. DHLA coated nanocrystals also exhibit high non-specific binding, rendering them unusable for single particle tracking applications. Ligand exchange with esters of DHLA with various length PEGs yielded nanocrystals that were highly stable in aqueous solution and suitable for live cell imaging (see, e.g, Uyeda, H. T.; et al., *J. Am. Chem. Soc.* 2005, 127, 3870-3878, which is incorporated by reference in its entirety). However, the hydroxyl-terminated surface of these DHLA-PEG nanocrystals lacks the functionality for efficient and selective covalent derivatization under mild conditions, for example with targeting biomolecules for receptor labeling on cells.

Two commonly employed nanocrystal derivatization strategies are direct covalent modification of nanocrystals using common bioconjugation methods such as 1-ethyl-3-(3-dimethylaminopropyl) carbodiimide (EDC) and N-hydroxysuccinimide (NHS) mediated cross-coupling between amino and carboxyl functionalities, and self-assembly of biomolecules onto nanocrystals via electrostatic or metal-affinity (such as His-tag) interactions. See, for example, Wu, X.; et al., *Nature Biotechnol.* 2003, 21, 41-46; Yan Zhang; et al., *Angew. Chem. Int. Ed.* 2006, 45, 4936-4940; and Goldman, E. R.; et al., *J. Am. Chem. Soc.* 2002, 124, 6378-6382, each of which is incorporated by reference in its entirety. Nanocrystals encapsulated in polymeric/phospholipid/silica shells are generally derivatized by covalent conjugation. Nanocrystals capped with DHLA or DHLA-PEG are amenable to conjugation using metal-affinity interactions between a $His_6$-tagged biomolecule and the metal surface of the nanocrystal, leading to stable conjugates that retain both nanocrystal luminescence and functionality of the coordinated biomolecules (see, e.g., Medintz, I. L., *Nature Mater.* 2003, 2, 630-638, which is incorporated by reference in its entirety).

A nanocrystal ligand can include a first portion that includes one or more coordinating atoms, a second portion including one or more hydrophilic groups, and a third portion including one or more ionizable groups. The coordinating atoms can be, for example, N, O, P, or S. The coordinating atoms can be included in a coordinating group, e.g., an amine, a nitroxide, an alcohol, a carboxylate, a thiocarboxylate, a phosphine, a phosphine oxide, a thiol, or the like. The hydrophilic groups can include, for example, an alkoxide, an amine, a thiol, an alcohol, a carboxylate, a ketone, an aldehyde, or the like. The ionizable group can be a group that has an electrostatic charge or one that can become electrostatically charged in an aqueous environment. Exemplary ionizable groups include amines (e.g., primary, secondary, tertiary and quaternary amines), carboxylates, alcohols, thiols, and the like.

Ligand exchanges can be carried out by one-phase or two-phase methods. Prior to ligand exchange, nanocrystals can be precipitated from their growth solutions by addition of methanol. The supernatant solution, which includes excess coordinating agent (e.g., trioctylphosphine), can be discarded. The precipitated nanocrystals can be redispersed in hexanes. Precipitation and redispersion can be repeated until essentially all the excess coordinating agent has been separated from the nanocrystals. A one-phase process can be used when both the nanocrystals and the ligands to be introduced are soluble in the same solvent. A solution with an excess of new ligands can be mixed with the nanocrystals. The mixture can be stirred at an elevated temperature until ligand exchange is complete. The one-phase method can be used, for example, to exchange octyl-modified oligomeric phosphines or methacrylate-modified oligomeric phosphines, which are both soluble in solvents that are compatible with the nanocrystals, such as hexanes. A two-phase ligand exchange process can be preferable when the nanocrystals and the new ligands do not have a common solvent. Nanocrystals can dissolved in an organic solvent such as dichloromethane, and the new ligand can be dissolved in an aqueous solution. The nanocrystals can be transferred from the organic phase to the aqueous phase by, for example, sonication. The transfer can be monitored through absorption and emission spectroscopy. similar two-phase ligand exchange process has been reported earlier. See, for example, Wang, Y. A., et al., 2002 *J. Am. Chem. Soc* 124, 2293, incorporated by reference in its entirety.

The nanocrystal can be a member of a population of nanocrystals having a narrow size distribution. The nanocrystal can be a sphere, rod, disk, or other shape. The nanocrystal can include a first semiconductor material, a ceramic material, a magnetic material, or a metallic material, for example, gold, iron oxide, titanium dioxide, cerium oxide or other metal chalcogenide or pnictide. The nanocrystal can include a first semiconductor material having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof. The first semiconductor material can include a Group II-VI compound, a Group II-V compound, a Group III-VI compound, a Group III-V compound, a Group IV-VI compound, a Group I-III-VI compound, a Group II-IV-VI compound, a Group II-IV-V compound, or mixtures thereof. For example, the first semiconductor material can include for example, ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof.

In some embodiments, the nanocrystal includes a first semiconductor material including a Group I-III-VI compound. For example, the first semiconductor material can include for example, a copper indium diselenide such as a doped copper indium diselenide or other copper indium diselenide, or alloyed copper indium diselenide, such as, for example, copper indium zinc diselenide, or copper indium gallium diselenide. The first semiconductor material can include a copper indium disulfide such as a doped copper indium disulfide or other copper indium disulfide, or alloyed copper indium disulfide. Other elements alloyed with copper indium diselenide and/or copper indium disulfide can include sulfur, aluminum, or silver; for example, $CuInS_2$, $CuIn(S,Se)_2$, $Cu(In,Al)Se_2$, $Cu(In,Ag)Se_2$, or others.

The nanocrystal can include a second semiconductor material. The second semiconductor material can a composition different from the composition of the first semiconductor material. The first and second semiconductor materials can be selected to provide a desired band structure, such as a type I or a type II heterostructure. The second semiconductor material can be adjacent to the first semiconductor material, such that a junction is formed. The junction can be abrupt or graded. In a graded junction, the first material blends with the second material in the junction, providing a graded change in material. In contrast, in an abrupt junction there is little or substantially no blending of the materials.

The second semiconductor material of the nanocrystal can include a Group II-VI compound, a Group II-V compound, a Group III-VI compound, a Group III-V compound, a Group IV-VI compound, a Group I-III-VI compound, a Group II-IV-VI compound, a Group II-IV-V compound, or mixtures thereof. For example, the second semiconductor material can include ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof. For example, ZnS, ZnSe or CdS overcoatings can be grown on CdSe or CdTe nanocrystals. In another example, ZnSe or CdSe overcoatings can be grown on InAs nanocrystals. In previous work with InAs core-shell semiconductor nanocrystals, the shell materials based on selenides were prone to oxidation, hindering stability and surface modifications. InAs core-shell materials based on the air-stable sulfides have been limited to the highly lattice mismatched ZnS shell. See, for example, Choi, H. S.; Ipe, B. I.; Misra, P.; Lee, J. H.; Bawendi, M. G.; Frangioni, J. V. *Nano Letters* 2009, 9, 2354-2359 and Cao, Y.; Banin, U. *J. Am. Chem. Soc.* 2000, 122, 9692-9702, each of which is incorporated by reference in its entirety.

An alloy can have the formula $M^1_iM^2_jM^3_kE^1_xE^2_yE^3_z$. $M^1$, $M^2$ and $M^3$ can each independently be a group I, group II, group III, or group IV element. $E^1$, $E^2$ and $E^3$ each independently can be a group IV, group V, or group VI element. For example, $M^1$, $M^2$ and $M^3$ can each independently be magnesium, zinc, copper, cadmium, mercury, aluminum, gallium, indium, thallium, silicon, germanium, tin, or lead; and $E^1$, $E^2$ and $E^3$ each independently can be silicon, germanium, tin, lead, nitrogen, phosphorus, arsenic, antimony, oxygen, sulfur, selenium, or tellurium.

In general, the values of i, j, k, x, y, and z are non-negative. In some instances, the value of i, j, k, x, y, or z can be an integer. For example, an alloy can have the formula $M^1E^1_xE^2_y$. In this formula, the value of i is 1 and the values of j and k are zero (alternatively, $M^1$, $M^2$ and $M^3$ are identical), and the value of z is zero (alternatively, $E^2$ and $E^3$ are identical). The sum of i, j and k can be an integer, and the sum of x, y and z can be an integer. For example, if the sum of x and y is 1, the preceding formula can be expressed as $M^1E^1_xE^2_{1-x}$. In another example, an alloy can have the formula $M^1_iM^2_{1-i}E^1$. An alloy can have the formula $M^1_iM^2_jM^3_kE^1_x$ or $M^1_iM^2_jM^3_kE^1_xE^2_y$.

A nanocrystal having a central region and a distal region (or regions) can be described by a radius ratio. The radius ratio can be defined as the ratio of the radius of the distal region to the radius of the central region. The central region can have a radius in the range of 1 nm to 7 nm (such as between 1.5 nm and 5 nm), and the distal regions can have a radius in the range of 1 nm to 10 nm (such as between 1.5 nm and 5 nm). Accordingly, a barbell-shaped nanocrystal can have a radius ratio in the range of 0.1 to 10 (such as between 0.3 and 3.5). In some embodiments the radius ratio can be about 1. In other embodiments it can be substantially different than about 1, such as, for example, between 0.1 and 0.95 or between 1.05 and 10.

The junction between two semiconductor materials can have different configurations depending on the shape of the nanocrystal. For example, a spherical nanocrystal can have a spherical core of a first semiconductor material coated with a shell of a second semiconductor material. A rod shaped nanocrystal can have a rod of a first semiconductor material and a second semiconductor material. The second semiconductor material can coat the length and ends of the rods substantially evenly. Alternatively, the length and ends of the rod can be coated to different degrees. In particular, the ends of the rod can coated to a greater degree than the length of the rod. The ends of the rod each can be coated by an approximately spherical region of a second semiconductor material. In this case, the nanocrystal can have a barbell shape.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, CdSe can be tuned in the visible region and InAs can be tuned in the infrared region.

The population of nanocrystals can have a narrow size distribution. The population can be monodisperse and can exhibit less than a 15% rms deviation in size of the nanocrystals, preferably less than 10%, more preferably less than 5%. Spectral emissions in a narrow range of between 10 and 150 nm full width at half max (FWHM) can be observed (in other words, FWHM of less than 0.05 eV, or of less than 0.03 eV). Semiconductor nanocrystals can have emission quantum efficiencies of greater than 2%, 5%, 10%, 20%, 40%, 60%, 70%, 80%, or 90%.

The method of manufacturing a nanocrystal can be a colloidal growth process and can produce a monodisperse particle population. Colloidal growth occurs by rapidly injecting one or more M donors and one or more E donor(s) into a hot coordinating agent. In another variation, the M donor(s) are dissolved in a hot coordinating agent, and E donor(s) are rapidly injected. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. Preparation and manipulation of nanocrystals are described, for example, in U.S. Pat. No. 6,322,901, which is incorporated by reference in its entirety.

The nanocrystal is a member of a population of nanocrystals. As a result of the discrete nucleation and controlled growth, the population of nanocrystals obtained can have a narrow, monodisperse distribution of sizes. The process of controlled growth and annealing of the nanocrystals in the coordinating agent that follows nucleation can also result in uniform surface derivatization and regular core structures. As the size distribution sharpens, the temperature can be raised to maintain steady growth. By adding more M donor or E donor, the growth period can be shortened.

The M donor(s) can be an inorganic compound, an organometallic compound (e.g., an alkyl metal compound such as triethyl gallium or trimethyl indium), or elemental metal. The inorganic compound can be a salt (e.g., a carboxylate salt, an acetylacetonate salt, a metal halide, a metal oxide, a metal alkoxide, and the like). In some cases, a metal carboxylate can include a long-chain hydrocarbon moiety, e.g., a $C_{10-30}$ alkyl, alkenyl, or alkynyl moiety, which can optionally include one or more cyclic (e.g., alicyclic, aryl) moieties. The salt can be combined with a coordinating agent, such as an amine. See, for example, U.S. Pat. No. 6,576,291, which is incorporated by reference in its entirety. M can be cadmium, zinc, copper, magnesium, mercury, aluminum, gallium, indium or thallium. The E donor(s) can be a compound capable of reacting with the M donor to form a material with the general formula $M^1_iM^2_jM^3_kE^1_xE^2_yE^3_z$. Typically, the E donor is a chalcogenide donor or a pnictide donor, such as a phosphine chalcogenide, a bis(silyl) chalcogenide, dioxygen, an ammonium salt, or a tris(silyl) pnictide. Suitable E donors include dioxygen, bis(trimethylsilyl) selenide ($(TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl)telluride ($(TMS)_2Te$), bis(trimethylsilyl)sulfide ($(TMS)_2S$), a trialkyl phosphine sulfide such as (tri-n-octylphosphine) sulfide (TOPS), an ammonium salt such as an ammonium halide (e.g., $NH_4Cl$), tris(trimethylsilyl) phosphide ($(TMS)_3P$), tris(trimethylsilyl) arsenide ($(TMS)_3As$), or tris(trimethylsilyl) antimonide ($(TMS)_3Sb$). In certain embodiments, the M donor and the E donor can be moieties within the same molecule.

A coordinating agent can help control the growth of the nanocrystal. The coordinating agent is a compound having a donor lone pair that, for example, has a lone electron pair available to coordinate to a surface of the growing nanocrystal. The coordinating agent can be a solvent. Solvent coordination can stabilize the growing nanocrystal. Typical coordinating agents include alkyl phosphines, alkyl phosphine oxides, alkyl phosphonic acids, or alkyl phosphinic acids, however, other coordinating agents, such as pyridines, furans, and amines may also be suitable for the nanocrystal production. Examples of suitable coordinating agents include pyridine, tri-n-octyl phosphine (TOP) and tri-n-octyl phosphine oxide (TOPO). Technical grade TOPO can be used.

Nanocrystal shape can be determined by synthesis conditions, notably by the coordinating solvent(s) present during nanocrystal synthesis. The nanocrystal can be a sphere, rod, disk, or other shape. See, e.g., U.S. Pat. Nos. 6,225,198; 6,306,736; and 6,855,202, each of which is incorporated by reference in its entirety. Nanocrystal shape can be further controlled by the conditions under which a second semiconductor material is added to the nanocrystal.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average size, a population having a desired average nanocrystal size can be obtained.

The particle size distribution can be further refined by size selective precipitation with a poor solvent for the nanocrystals, such as methanol/butanol as described in U.S. Pat. No. 6,322,901, incorporated herein by reference in its entirety. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean size, preferably 10% rms deviation or less, and more preferably 5% rms deviation or less.

A cap including a second semiconductor material can be added to the nanocrystal. A capping process is described, for example, in U.S. Pat. No. 6,322,901, which is incorporated by reference in its entirety. By adjusting the temperature of the reaction mixture during capping and monitoring the absorption spectrum of the core, capped materials having high emission quantum efficiencies and narrow size distributions can be obtained. The shape of the cap can depend on the shape of the initial nanocrystal and the capping conditions used. For example, a cap grown on an approximately spherical nanocrystal can also be approximately spherical. In this case, the cap can substantially coat the spherical nanocrystal. If the initial nanocrystal is rod-shaped, the cap can be grown primarily on the ends of the rod and very little of the second semiconductor material added along the axis of the rod. A rod-shaped nanocrystal can be capped with a rod-shaped cap, or with an approximately spherical cap. Capping conditions, such as solvent composition and temperature, can determine the shape of the cap. For example, when caps are added under conditions that favor rod-shaped growth, rod-shaped caps can be formed; in contrast, approximately spherical caps are formed when the capping conditions favor approximately spherical growth.

It can be advantageous to purify nanocrystals before a second material is added to the nanocrystal. As discussed above, the nanocrystals can be purified by size-selective precipitation. After purification the nanocrystals can be treated with an etching agent. The etching agent can reduce the number of defect sites on the nanocrystals. Defect sites can act as undesired nucleation sites during addition of a second material. In making barbell-shaped nanocrystals, nucleation is desired at the ends of rods, but defect sites can cause nucleation along the length of a rod. Because the etching agent reduces the number of defect sites, the resulting barbells will have fewer warts along the length of the rods than barbells prepared without a prior etching treatment. The etching agent can be an amine, such as a primary amine, e.g., octylamine. An etching agent can be included during addition of a second semiconductor material to a nanocrystal.

Transmission electron microscopy (TEM) can provide information about the size, shape, and distribution of the nanocrystal population. Powder X-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from X-ray diffraction data using, for example, the Scherrer equation. It also can be estimated from the UV/Vis absorption spectrum.

The outer surface of the nanocrystal can include a layer of compounds derived from the coordinating agent used during the growth process. The surface can be modified by repeated exposure to an excess of a competing coordinating group to form an overlayer. For example, a dispersion of the nanocrystal can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

In general, a ligand for a nanocrystal can include a first monomer unit including a first moiety having affinity for a surface of the nanocrystal, a second monomer unit including a second moiety having a high water solubility, and a third monomer unit including a third moiety having a selectively reactive functional group or a selectively binding functional group. In this context, a "monomer unit" is a portion of a polymer derived from a single molecule of a monomer. For example, a monomer unit of poly(ethylene) is —$CH_2CH_2$—, and a monomer unit of poly(propylene) is —$CH_2CH(CH_3)$—. A "monomer" refers to the compound itself, prior to polymerization, e.g., ethylene is a monomer of poly(ethylene) and propylene of poly(propylene).

A selectively reactive functional group is one that can form a covalent bond with a selected reagent under selected conditions. One example of a selectively reactive functional group is a primary amine, which can react with, for example, a succinimidyl ester in water to form an amide bond. A selectively binding functional group is a functional group that can form a noncovalent complex with a selective binding counterpart. Some well known examples of selectively binding functional groups and their counterparts include biotin and streptavidin; a nucleic acid and a sequence-complementary nucleic acid; FK506 and FKBP; or an antibody and its corresponding antigen.

A moiety having high water solubility typically includes one or more ionized, ionizable, or hydrogen bonding groups, such as, for example, an amine, an alcohol, a carboxylic acid, an amide, an alkyl ether, a thiol, or other groups known in the art. Moieties that do not have high water solubility include, for example, hydrocarbyl groups such as alkyl groups or aryl groups, haloalkyl groups, and the like. High water solubility can be achieved by using multiple instances of a slightly soluble group: for example, diethyl ether is not highly water soluble, but a poly(ethylene glycol) having multiple instances of a —$CH_2$—O—$CH_2$— alkyl ether group can be highly water soluble.

For example, the ligand can include a polymer including a random copolymer. The random copolymer can be made using any method of polymerization, including cationic, anion, radical, metathesis or condensation polymerization, for example, living cationic polymerization, living anionic polymerization, ring opening metathesis polymerization, group transfer polymerization, free radical living polymerization, living Ziegler-Natta polymerization, or reversible addition fragmentation chain transfer (RAFT) polymerization. The random copolymer can include regions having each of the following formulae:

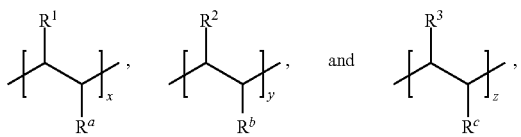

In these regions, $R^1$ is a first moiety having affinity for a surface of the nanocrystal, $R^2$ is a second moiety having a high water solubility, $R^3$ is a third moiety having a selectively reactive functional group or a selectively binding functional group, each of $R^a$, $R^b$, and $R^c$, independently, is substituted or unsubstituted alkyl, substituted or unsubstituted alkoxy, substituted or unsubstituted aryl, or substituted or unsubstituted aryloxy; and each of x, y, and z, independently, a positive integer.

Polyhistidine motifs can have high affinity a nanocrystal surface (e.g., when the surface includes Cd and/or Zn, or other Group II elements), and $His_6$-tags have been employed for facile and efficient derivatization of nanocrystals with peptides, dyes, and proteins. See, for example, Howarth, M.; Liu, W.; Puthenveetil, S.; Zheng, Y.; Marshall, L. F.; Schmidt, M. M.; Wittrup, K. D.; Bawendi, M. G.; Ting, A. Y., Monovalent, reduced-size quantum dots for imaging receptors on living cells. *Nat Meth* 2008, 5, (5), 397-399; Sapsford, K. E.; Pons, T.; Medintz, I. L.; Higashiya, S.; Brunel, F. M.; Dawson, P. E.; Mattoussi, H., Kinetics of Metal-Affinity Driven Self-Assembly between Proteins or Peptides and CdSe-ZnS Quantum Dots. *J. Phys. Chem. C.* 2007, 111, (11528-11538); Medintz, I. L.; Pons, T.; Delehanty, J. B.; Susumu, K.; Brunel, F. M.; Dawson, P. E.; Mattoussi, H., Intracellular delivery of quantum dot-protein cargos mediated by cell penetrating peptides. *Bioconjugate Chemistry* 2008, 19, (9), 1785-1795; and Aaron R. Clapp, I. L. M., Hedi Mattoussi, Förster Resonance Energy Transfer Investigations Using Quantum-Dot Fluorophores. *ChemPhysChem* 2006, 7, (1), 47-57, each of which is incorporated by reference in its entirety.

A polymer rich with imidazole groups can achieve efficient and multi-dentate binding to a nanocrystal surface. The polyimidazole motif can be advantageous because it is not susceptible to the issues plaguing thiol-based chemistry, such as degradation by oxidation. Furthermore, multidentate binding by a polyhistidine can greatly enhance stability. See, for example, Yildiz, I.; McCaughan, B.; Cruickshank, S. F.; Callan, J. F.; Raymo, F. i. M., Biocompatible CdSe-ZnS Core-Shell Quantum Dots Coated with Hydrophilic Polythiols. *Langmuir* 2009, 25, (12), 7090-7096, which is incorporated by reference in its entirety. To promote water solubility and reduce non-specific binding, a PEG derived monomer can be co-polymerized along with an imidazole-based monomer to form a co-polymer displaying both PEG and imidazole groups along the backbone. See, for example, Bentzen, E. L.; Tomlinson, I. D.; Mason, J.; Gresch, P.; Warnement, M. R.; Wright, D.; Sanders-Bush, E.; Blakely, R.; Rosenthal, S. J., Surface modification to reduce nonspecific binding of quantum dots in live cell assays. *Bioconjugate Chemistry* 2005, 16, (6), 1488-1494, which is incorporated by reference in its entirety. Using an additional monomer featuring an amine or a biotin functional group, a 3-component multi-functional co-polymer can be synthesized for nanocrystal water solubilization and derivatization.

Radical addition fragmentation chain transfer (RAFT) polymerization chemistry can provide molecular weight control and narrow polydispersity of the co-polymer. The RAFT agent can also mediate polymerization of a wide diversity of monomers for controlled co-polymerization. See, for example, Chiefari, J.; Chong, Y. K.; Ercole, F.; Krstina, J.; Jeffery, J.; Le, T. P. T.; Mayadunne, R. T. A.; Meijs, G. F.; Moad, C. L.; Moad, G.; Rizzardo, E.; Thang, S. H., Living free-radical polymerization by reversible addition-fragmentation chain transfer: The RAFT process. *Macromolecules* 1998, 31, (16), 5559-5562, which is incorporated by reference in its entirety. By tuning the ratio and composition of monomers, complex co-polymers can be assembled with the desired properties for nanocrystal water solubilization and derivatization, form compact nanocrystals suitable for live cell and in-vivo imaging with extremely low non-specific binding and greatly enhanced stability and long-term shelf-life. By using a catechol group instead of imidazole for binding, iron oxide nanocrystals can also be solublized. The length of PEG chain can be chosen in part based on the size of the nanocrystal involved—larger nanocrystals can require longer PEG chains for solubility.

EXAMPLE 1

The synthesis of small InAs cores (1.4 nm inorganic diameter) was carried out in a mixture of octadecene, tri-n-octyl phosphine (TOP), tris(trimethylsilyl) arsine, and indium myristate using a slightly modified version of the synthesis reported by Xie and Peng. See, for example, Xie, R.; Peng, X. *Angew. Chem.* 2008, 47, 7677-7680, which is incorporated by reference in its entirety. Unless otherwise specified, all reagents were obtained from Sigma. All solvents were spectrophotometric grade and obtained from EMD Biosciences. Nanocrystal synthesis was performed using standard air free techniques on a nitrogen filled Schlenk line. All glove-box manipulations were performed in an mBraun box (<0.1 ppm oxygen) or VAC box (<0.5 ppm oxygen).

0.15 mmol of indium acetate (99.99, Alfa Aesar), 0.45 mmol of myristic acid (99.5%, Sigma), and 3 ml of octadecene (90%, Sigma) were added to a four neck 25 ml round bottom flask. The solution was heated to 100° C. under vacuum for one hour. The reaction mixture was then placed under nitrogen and heated to 150° C. A solution of 0.125 mmol of tris(trimethylsilyl)arsine (Nanomeps, France) and 0.75 ml of tri-n-octylphosphine (97%, Strem) was prepared (under minimal lighting) in a nitrogen filled glovebox. This solution was then swiftly injected into the reaction flask and the temperature was increased to 230° C. for twenty minutes.

Oleyl amine was added prior to shell growth to provide surface passivation during the over-coating process. In FIG. 6A the resulting enhancement of quantum yield is shown. After the synthesis of the InAs cores, the reaction flask was cooled to 170° C. and 3 ml of dry oleyl amine (Acros Organics) was injected (addition of over-coating precursors began immediately after the injection of amines). Oleyl amine was degassed under vacuum at 120° C. for two hours prior to use.

For shell growth, solution A was prepared by adding 1 mmol of bis(trimethylsilyl)sulfide to 10 ml of tri-n-octyl phosphine. Solution B was prepared by adding 0.34 mmol of dimethyl cadmium and 0.66 mmol of diethyl zinc to 10 ml of tri-n-octyl phosphine. Dimethyl cadmium and diethyl zinc were passed through a 20 nm filter prior to use. Solution A and B were added simultaneously via syringe pump to the reaction flask at the rate of 1.5 ml/hour. The reaction was stopped when the peak photoluminescence reached ~800 nm.

FIG. 1 demonstrates water solubilization of InAs(ZnCdS) nanocrystals through ligand exchange with a polymeric imidazole ligand (PIL). Poly(amino-$PEG_{11}$)$_{25\%}$-PIL is a random co-polymer built on an acrylic acid backbone incorporating poly(ethylene) glycol ($PEG_{12}$) groups for water solubility (25 mol %), amino-$PEG_{11}$ groups for conjugation chemistry (25 mol %), and imidazole groups for QD binding (50 mol %), the detailed synthesis and characterization of these polymers is reported elsewhere. See, for example, provisional U.S. Patent Application No. 61/234,305, filed Aug. 16, 2009, which is incorporated by reference in its entirety. In FIG. 5B, the resulting aqueous nanocrystals have a hydrodynamic diameter (HD) of <10 nm. The QYs of ligand exchanged nanocrystals were typically 25%. In FIGS. 2C-2D, the absorption spectrum remained identical before and after ligand exchange, and the small decrease in PL was consistent with a high quality shell.

InAs(ZnCdS) nanocrystals were ligand exchanged with the amine functionalized poly(amino-$PEG_{11}$)$_{25\%}$-PIL polymer. For ligand exchange, nanocrystals (2 nmol) were precipitated 1× using a mixture of acetone and butanol and brought into 50 μL of $CHCl_3$. The nanocrystal stock solution was added to a solution of poly(PEG)-PIL (5 mg) in $CHCl_3$ (30 μL), and stirred for 10 min at RT, after which 30 μL of MeOH was added followed by stirring for an additional 40 min. Nanocrystal samples were precipitated by the addition of EtOH (30 μL), $CHCl_3$ (30 μL), and excess hexanes. The sample was centrifuged at 4000 g for 2 min, the supernatant discarded, and the pellet precipitated once more by the addition of EtOH, $CHCl_3$, and excess hexanes. After centrifugation and removal of the supernatant, the pellet was dried in vacuo, and PBS (500 μL, pH 7.4) was added, followed by filtration through a 0.2 μm filter.

The primary amines allow for streptavidin to be coupled to the nanocrystals by a 1-ethyl-3-(3-dimethylaminopropyl) carbodiimide (EDC) coupling scheme to create a streptavidin-nanocrystal construct. For covalent conjugation of streptavidin to poly(aminoPEG$_{11}$)$_{25\%}$, commercial SA (50 μL, 10 mg/mL) was activated in MES buffer (pH 6.5) using Sulfo-NHS and EDC (20 eq.) for 20 min at RT. The activated SA was mixed with poly(aminoPEG$_{11}$)$_{25\%}$ nanocrystals in sodium bicarbonate buffer at pH 8.4 at a SA:nanocrystal ratio of 5:1 and allowed to react for 1 hr. The samples were dialyzed 2× though a 50 kDa MW cut-off spin concentrator and then used for labeling experiments. The shell thickness and ZnCdS composition can be precisely tuned by reaction time and reagent concentrations. In FIG. 2A-D, it is shown that 2.5 monolayers of $Zn_{0.7}Cd_{0.3}S$ provided small nanocrystals (2.9 nm inorganic diameter) with emission at 800 nm (QY 35-50%) that retain high QY when ligand exchanged. The QY of 800 nm emitting InAs(ZnCdS) nanocrystals was measured relative to 1,1',3,3,3',3'-hexamethylindotrycarbocyanine iodide (HITC, QY=26%) ($\lambda_{ex}$=680 nm). Solutions of nanocrystals in PBS and dye in methanol were optically matched at the excitation wavelength. Quantum yields were calculated from the following expression: $QY_{nanocrystal} = QY_{Dye} \times (Absorbance_{dye}/Absorbance_{nanocrystal}) \times (Peak\ Area_{nanocrystal}/Peak\ Area_{Dye}) \times (n_{nanocrystal\ solvent})^2/(n_{Dye\ solvent})^2$.

HeLa cells were transfected with a plasmid for yellow fluorescent protein (YFP), bound to an extracellular acceptor peptide (AP) tag and a transmembrane domain (TM) for cell surface targeting (AP-YFP-TM), as well as with a plasmid for endoplasmic reticulum-localized biotin ligase (BirA). HeLa cells were grown in DMEM (Mediatech) with 10% Fetal Bovine Serum (Invitrogen), 50 U/mL penicillin and 50 μg/mL streptomycin (Invitrogen). Transfection plasmids were a kind gift from A. Ting (MIT, US). The cells were transfected using 1 μl Lipofectamine 2000 (Invitrogen), 0.2 μg of BirA-ER and 0.2 μg of AP-YFP-TM per well of an 8-well chamber slide (LabTek). 1 mM biotin was added to the media during plasmid expression. Cells were imaged under 4° C. PBS the day after transfection. 1% Bovine Serum Albumin (Sigma) was added to block non-specific binding during specific binding studies of ligand-coated quantum dots. Commercial BSA is known to contain biotin, and the stock BSA solution was dialyzed with a 3 kDa cutoff dialysis tube three times for 8 h in PBS pH 7.4, in 4° C. See, for example, Liu, W.; Greytak, A. B.; Lee, J.; Wong, C. R.; Park, J.; Marshall, L. F.; Jiang, W.; Ting, A. Y.; Nocera, D. G.; Fukumura, D.; Jain, R. K.; Bawendi, M. G. *J. Am. Chem. Soc.* 2009, submitted; Howarth, M.; Takao, K.; Hayashi, Y.; Ting, A. Y. *Proc Natl Acad Sci USA.* 2005, 102, 7583-7588; Howarth, M.; Liu, W.; Puthenveetil, S.; Zheng, Y.; Marshall, L. F.; Schmidt, M. M.; Wittrup, K. D.; Bawendi, M. G.; Ting, A. Y. *Nat Meth* 2008, 5, 397-399; and Howarth, M.; Ting, A. Y. *Nature Protocols* 2008, 3, 534-545, each of which is incorporated by reference in its entirety.

The AP tag is specifically biotinylated by the co-expressed BirA and displayed on the cell surface as a fusion to YFP and the TM domain. FIG. 3A shows that no non-specific cell interactions occurred when biotin blocked streptavidin-nanocrystal conjugates were incubated with HeLa cells. In FIG. 3B co-localization of the YFP and NIR streptavidin-nanocrystal signal was observed, indicating targeting of streptavidin-nanocrystals to the biotin at the cell membrane.

For in vivo applications, the minimal absorption and auto-fluorescence in tissue in the NIR region suggest utility for NIR nanocrystals in intra-vital microscopy as high-contrast probes. In vivo imaging was carried out using a custom-built multiphoton microscope (Olympus) with a Ti:Sapphire excitation laser at 850 nm (Mai-Tai HP, Spectra-Physics) and a 20×0.95 NA water-immersion lens (Olympus). Mammary fat pad window chambers were implanted in female SCID mice as described previously. E0771 mammary tumors were implanted in the mammary fat pad in these chambers, and were allowed to grow for two weeks until the tumors were roughly 3 mm in diameter and well-vascularized. See, for example, Vakoc, B. J.; Lanning, R. M.; Tyrrell, J. A.; Padera, T. P.; Bartlett, L. A.; Stylianopoulos, T.; Munn, L. L.; Tearney, G. J.; Fukumura, D.; Jain, R. K.; Bouma, B. E. *Nat Med* 2009, *advance online publication*, which is incorporated by reference in its entirety. To determine appropriate concentrations for equal photoluminescence intensity for green visible CdSe (CdS) and NIR InAs(ZnCdS) nanocrystals in solution, multiphoton imaging of mixed solutions of these nanocrystals in glass microslides (VitroCom) was conducted. A mixture at these concentrations was then prepared, and 200 μL of this solution was injected intravenously into the mouse via a bolus retro-orbital injection. An image mosaic was then collected for the entire tumor, at depths from 0-200 μm into the tissue.

The effectiveness of green visible CdSe(CdS) was compared with NIR InAs(ZnCdS) nanocrystals as imaging agents for fluorescent angiography, in vivo, in a mouse model. Mammary fat pad window chambers were implanted in female SCID mice to facilitate fluorescence microscopy in living mammary tissue using multi-photon microscopy (MPM). See, for example, Brown, E. B.; Campbell, R. B.; Tsuzuki, Y.; Xu, L.; Carmeliet, D.; Fukumura, D.; Jain, R. K. *Nat. Med.* 2001, 7, 864-868, which is incorporated by reference in its entirety. E0771 mammary tumor cells were implanted and the tumors were allowed to grow to a diameter of 3 mm prior to imaging. In FIG. 5B, each nanocrystal sample was ligand exchanged with poly(PEG$_{12}$)-PIL, a polymer composed of PEG$_{12}$ (50 mol %) and imidazole (50 mol %), to achieve a HD<10 nm and a PEGylated surface to prevent non-specific binding. Using MPM, the green and NIR nanocrystals were adjusted to concentrations of equal PL intensities in vitro and injected 200 μL of this solution intravenously into the mouse via a bolus retro-orbital injection.

In FIG. 4, grayscale images of a mammary tumor in vivo were collected thirty minutes after intravenous injection of the green and NIR nanocrystals. The NIR nanocrystals clearly imaged deep vasculature up to 200 μm, while the visible emitting nanocrystals produce an image with poor vascular contrast and low PL intensity. FIG. 4A shows a region of the tumor with low levels of auto-fluorescence, and demonstrated rapidly decreasing vascular intensity with imaging depth for visible nanocrystals. NIR nanocrystals, on the other hand, were intense even at 200 μm as the emitted NIR light was absorbed less by the tissue than visible light. FIG. 4B shows a region of the tumor where high levels of auto-fluorescence resulted in poor contrast even at superficial depths for the visible nanocrystals. The NIR nanocrystals showed excellent contrast at all depths. The injected concentrations and microscopy parameters were maintained from in vitro imaging, and thus any differences in PL intensity and contrast between the two nanocrystals in vivo were the result of photon absorption and auto-fluorescence in surrounding tissues.

TEM measurements were performed on a JEOL200CX microscope. The InAs(ZnCdS) nanocrystals in water were dropped onto a Ted Pella ultra-thin carbon type A grid. Samples for wavelength dispersive spectroscopy were prepared by precipitating the nanocrystals from solution three times with a mixture of hexanes, butanol, and acetone. The nanocrystals were then drop-cast onto doped silicon substrates and analyzed on a JEOL 8200 scanning electron microscope. Gel filtration chromatograph (GFC) was performed using an ÄKTAprime Plus chromatography system from Amersham Biosciences equipped with a self-packed Superdex 200 10/100 column. PBS (pH 7.4) was used as the mobile phase with a flow rate of 1.0 mL/min. Detection was achieved by measuring the absorption at 280 nm.

EXAMPLE 2

CdSe cores were synthesized according to previously reported procedures and were overcoated with a CdS shell. See, for example, Murray, C. B.; Norris, D. J.; Bawendi, M. G. *J. Am. Chem. Soc.* 1993, 115, 8706-8715; Snee, P. T.; Chan, Y.; Nocera, D. G.; Bawendi, M. G. *Adv. Mater.* 2005, 17, 1131-1136; and Liu, W.; Howarth, M.; Greytak, A. B.; Zheng, Y.; Nocera, D. G.; Ting, A. Y.; Bawendi, M. G. *J. Am. Chem. Soc.* 2008, 130, 1274-1284, each of which is incorporated by reference in its entirety. For pure CdS shells, a successive ion layer adsorption and reaction (SILAR) procedure, modified from those reported by Peng et al. and Mews et al., was used. See, for example, Xie, R.; Kolb, U.; Li, J.; Basche, T.; Mews, A. *J. Am. Chem. Soc.* 2005, 127, 7480-7488 and Li, J. J.; Wang, Y. A.; Guo, W. Z.; Keay, J. C.;

Mishima, T. D.; Johnson, M. B.; Peng, X. G. *J. Am. Chem. Soc.* 2003, 125, 12567-12575, each of which is incorporated by reference in its entirety. Briefly, CdSe cores with a first exciton feature at 491 nm were synthesized by heating a mixture of trioctylphosphine (TOP), trioctylphosphine oxide (TOPO), CdO (0.9 mmol), and tetradecylphosphonic acid (TDPA, 2.0 mmol) to 340° C. under nitrogen, removing evolved water in vacuo at 160° C., re-heating to 360° C. under nitrogen, and rapidly introducing trioctylphosphine selenide (TOPSe, 3.4 mmol) in trioctylphosphine (TOP), followed by cooling to room temperature. Cores isolated by repeated precipitations from hexane with acetone were brought to 180° C. in a solvent mixture of oleylamine (3 mL) and octadecene (6 mL). Aliquots of Cd and S precursor solutions were then introduced alternately starting with the metal (Cd), waiting 15 min between the start of each addition. The Cd precursor consisted of 0.6 mmol Cd-oleate and 1.2 mmol decylamine in a solvent mixture of octadecene (3 mL) and TOP (3 mL). The S precursor consisted of 0.6 mmol hexamethyldisilathiane [$(TMS)_2S$] in 6 mL TOP. The dose of each over-coating precursor aliquot was calculated to provide a single monolayer of ions to the nanocrystal surface. Addition of a total of 4 aliquots each of Cd and S yielded nanocrystals with emission at 562 nm and a QY close to unity when diluted in hexane. See, for example, provisional U.S. Patent Application No. 61/234,305, filed Aug. 16, 2009, which is incorporated by reference in its entirety.

Other embodiments are within the scope of the following claims.

What is claimed is:

1. A composition for biological imaging comprising a water soluble semiconductor nanocrystal having a hydrodynamic diameter of no greater than 10 nm and having a peak emission wavelength in the range of 700 nm to 1000 nm and having a quantum efficiency of greater than 10%, wherein the semiconductor nanocrystal includes a polymeric ligand, and wherein the polymeric ligand is poly(amino-$PEG_{11})_{25}$%-PIL ligand.

2. The composition of claim 1, wherein the semiconductor nanocrystal has a core including a first semiconductor material, wherein the first semiconductor material is a III-V semiconductor.

3. The composition of claim 2, wherein the core has a diameter of 1.4 nm or less.

4. The composition of claim 2, wherein the semiconductor nanocrystal includes a shell on a surface of the core, the shell including a second semiconductor material, wherein the second semiconductor material is a II-VI semiconductor.

5. The composition of claim 4, wherein the II-VI semiconductor includes a II-VI semiconductor alloy.

6. The composition of claim 5, wherein the first semiconductor material is InAs and the II-VI semiconductor alloy is a ZnCdS alloy.

7. The composition of claim 1, wherein the quantum efficiency of the semiconductor nanocrystal is greater than 20%, 40%, 60%, 70%, or 80%.

* * * * *